United States Patent [19]

Shurmer

[11] Patent Number: 4,907,441

[45] Date of Patent: Mar. 13, 1990

[54] APPARATUS AND METHOD FOR IDENTIFYING OR MEASURING GAS OR LIQUID BORNE SUBSTANCES

[75] Inventor: Harold V. Shurmer, Rugby, England

[73] Assignee: National Research Development Corporation, London, England

[21] Appl. No.: 236,936

[22] Filed: Aug. 26, 1988

[51] Int. Cl.⁴ .............................................. G01N 31/00
[52] U.S. Cl. ........................................................ 73/23
[58] Field of Search ................. 73/23, 23.1, 27 R, 53

[56] References Cited

U.S. PATENT DOCUMENTS

| | | | |
|---|---|---|---|
| 4,384,283 | 5/1983 | Drope et al. | 73/23 X |
| 4,399,687 | 8/1983 | Collins | 73/23 |
| 4,457,161 | 7/1984 | Iwanaga et al. | 73/23 |
| 4,542,640 | 9/1985 | Clifford | 73/23 |
| 4,638,443 | 1/1987 | Kaneyasu et al. | 73/23 X |
| 4,759,210 | 7/1988 | Wohltjen | 73/23 |

FOREIGN PATENT DOCUMENTS 0089470 9/1983 European Pat. Off. .
88/00341 1/1988 PCT Int'l Appl. .

OTHER PUBLICATIONS

"Analysis of Discrimination Mechanisms in the Mammalian Olfactory System Using a Model Nose", Nature, vol. 299, No. 5881, pp. 352-355 (Persaud and Dodd).

Primary Examiner—Hezron E. Williams
Assistant Examiner—Joseph W. Roskos
Attorney, Agent, or Firm—Cushman, Darby & Cushman

[57] ABSTRACT

In apparatus for detecting or identifying gas or liquid or for measuring their concentration, an array of sensors arranged for simultaneous exposure to a substance is coupled to electrical circuitry arranged to generate electrical signal values which are linearly related to substance concentration. The sensors are selected to respond differently to a known sample substance or substances. By feeding the signal values to a processor programmed to combine the signal value in a series of linear equations, a series of output values are obtained which are characteristic of the sensed substance or substances which, when compared with stored data allow identification of the sensed substance or substances and the measurement of substance concentration.

10 Claims, 1 Drawing Sheet

APPARATUS AND METHOD FOR IDENTIFYING OR MEASURING GAS OR LIQUID BORNE SUBSTANCES

BACKGROUND TO THE INVENTION

This invention relates to apparatus and a method for identifying measuring or detecting gas or liquid borne substances which may be gases, vapours, liquids or solids.

Several attempts have been made to construct a device which can sense and distinguish various gases and vapours, such devices being of potential importance in the food and drink industries, in the analysis of perfumes, and in diagnostic medicine, amongst other uses. These devices have used sensors which respond to a variety of gases, liquids or particulate solids (such as solids present in smoke), but have predominantly been operated in environments where a particular class of chemical is to be detected, in each case the chemical being the only substance in the relevant environment to which the sensor is sensitive. It is also known to use sensors which respond to one specific compound class. However, in recent years there have been proposals for a device thought to be modelled on the mammalian nose, having a plurality of sensors which are each responsive to a wide variety of chemicals, but which respond differently from each other to those chemicals. By monitoring the outputs of the sensors together, it is possible to identify substances from the pattern of the outputs. The effect of varying concentrations can be largely avoided by monitoring the relative magnitudes of the sensor outputs, for example by analysing the ratios of pairs of outputs. A device of this form is outlined in a paper by Persaud and Dodd in 'Nature', Volume 299 at page 352 (Sept. 23, 1982). One of the main drawbacks of the approach adopted by Persaud and Dodd is the complexity of the pattern recognition process when the outputs of several sensors are to be analysed, and it is an object of the present invention to provide apparatus and a method which allow simpler analysis.

SUMMARY OF THE INVENTION

According to one aspect of this invention, apparatus for identifying, detecting, or measuring a gas or liquid borne substance or substances comprises an array of sensors arranged for simultaneous exposure to a substance, and electrical circuit means associated with the sensors and arranged to compensate for non-linear output versus substance concentration characteristics of the sensors whereby each sensor, in combination with the circuit means, is operable to generate an electrical signal having a characteristic which is linearly related to the concentration of a plurality of substances sensed by the sensor, the circuit means including means for processing the said signals to produce an electrical output indicative of the identity of the substance or substances sensed by the sensors or of the presence and/or concentration of a particular substance or substances. To produce different patterns of electrical signals when the sensors are exposed to different substances, the sensors are selected to respond differently from each other to known sample substances. By arranging for the electrical signals to be linearly related to substance concentrations, it is possible to combine the signal values in a series of linear equations in the processing means using, for example, simple matrix algebra.

Typically, the electrical circuit means include input circuitry having a resistive or capacitive potential divider connectible to the sensors via a multiplexing switch arrangement, or several such dividers each coupled to a respective sensor. If the sensors themselves do not exhibit linear output versus concentration characteristics, the input circuitry may include characteristic conversion circuitry such as an anti-log amplifier in the case of the sensors exhibiting a logarithmic characterisic. Other non-linear sensor characteristics may be converted to yield resultant linear characteristics in a similar manner. The circuit means preferably further comprises an analogue-to-digital converter for providing digital representations of the sensor outputs for feeding to a microcomputer acting as the processing means. Linear analysis of the digital representations may then be performed to produce not only an output indicative of substance identity, but also of substance concentration, this output being fed to a display device. It is possible for the processing means itself to form part of the circuit means that produce electrical signals linearly related to the sensor outputs, insofaras conversion of the sensor outputs to digital form may take place before compensation for sensor non-linearity takes place in the microcomputer under the control of the computer program.

From a method aspect, the invention includes a method of identifying, detecting, or measuring a gas or liquid borne substance or substances comprising providing an plurality of sensors which respond differently from each other to given substances, arranging for the sensors each to be exposed to the substance or substances to be identified, detected or measured, feeding electrical outputs from the sensors to electrical circuitry to generate a plurality of electrical signal values related to substance concentration, said electrical circuitry compensating for non-linear output versus substance concentration characteristics of the sensors whereby said signal values are linearly related to substance concentration, and performing a mathematical operation on the said signal values to generate information relating to the identity or presence of the substance to be identified or detected and/or the concentration of the said substance.

The particular form of the preferred apparatus may vary according to the substances to be detected and according to whether the substances are gases, vapours, liquids, or particulate solids, and gas or liquid borne.

BRIEF DESCRIPTION OF THE DRAWINGS

The invention will now be described by way of example with reference to the drawings in which.

DETAILED DESCRIPTION OF PREFERRED EMBODIMENTS OF THE INVENTION

Figure 1:
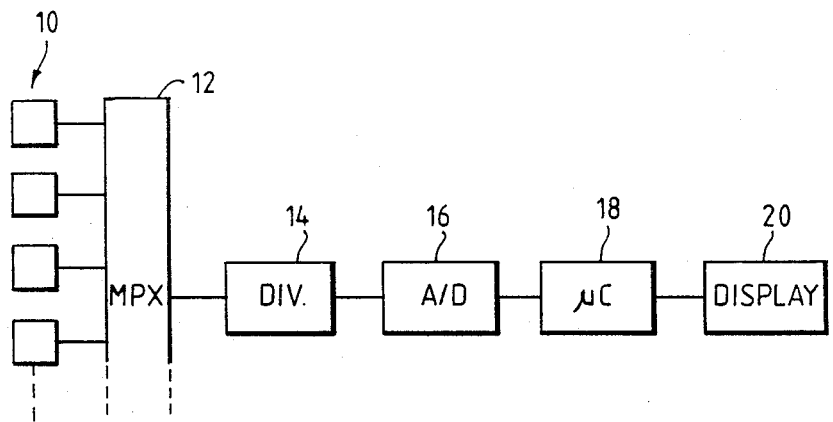
FIG. 1 is a block diagram of a first model "nose" in accordance with the invention.

Referring to FIG. 1, a electronic model "nose" having properties akin to that of the mammalian olfactory system has a plurality of sensors arranged in an array 10 so that the sensors may be exposed simultaneously to a substance to be identified or detected. Each sensor has a response characteristic which is different from those of the other sensors over a wide range of detectable odorants, so that different patterns of electrical outputs are generated when the array 10 is exposed to different substances, or mixtures of substances.

In the embodiment of FIG. 1, the sensors are coupled to a multiplexer 12 which sequentially couples each sensor in turn to a load element or potential divider element 14, the precise form of which depends on the nature of the sensors used. This element may also comprise a circuit which compensates for non-linear sensor characteristics. For instance, it may form one arm of a potential divider, the arm having a non-linear impedance characteristic, or it may include an operational amplifier circuit with a non-linear transfer function. In any event, the element 14 in combination with each sensor produces an electrical signal having a characteristic, e.g. voltage, which varies linearly with substance concentration over a predetermined range.

The load or divider element 14 is coupled to an A to D converter 16 which is in turn coupled to an input port of a microcomputer 18. It will be appreciated that, with the combined operation of the multiplexer 12, element 14, and converter 16, the microprocessor is presented with a series of digital samples each representing a particular sensor and each having a value which is linearly related to the concentration of a substance or substances to which the array of sensors 10 is exposed. The value of each sample may therefore be expressed by the linear equation:

$$V_n = a_n C_1 + b_n C_2 + c_n C_3 + \ldots$$

where $V_n$ is the value yielded by a sensor n, $C_1$, $C_2$, etc. are the concentration of first, second, third etc. substances, and $a_n$, $b_n$, $c_n$, etc. are constants characteristic of the sensor n. When the microcomputer 18 has received and stored a complete set of such samples corresponding to the whole array of sensors, the resulting set of linear equations may be solved by relatively straightforward calculation based on the principle of superposition. In this way, under the control of the program, values of $C_1$, $C_2$, $C_3$, etc. are yielded, provided that the computer is given values for the coefficients $a_n$, $b_n$, etc., which would be obtained by exposing the array 10 to known "doses" of selected known substances. Indeed, the computer 18 can be programmed to calculate and "learn" the coefficients associated with the particular array of sensors to which it is connected.

Having obtained values for $C_1$, $C_2$, $C_3$, etc., it is then possible to display the result in a display 20 coupled to the computer as, for example, a list of substances and their concentrations.

Figure 2:
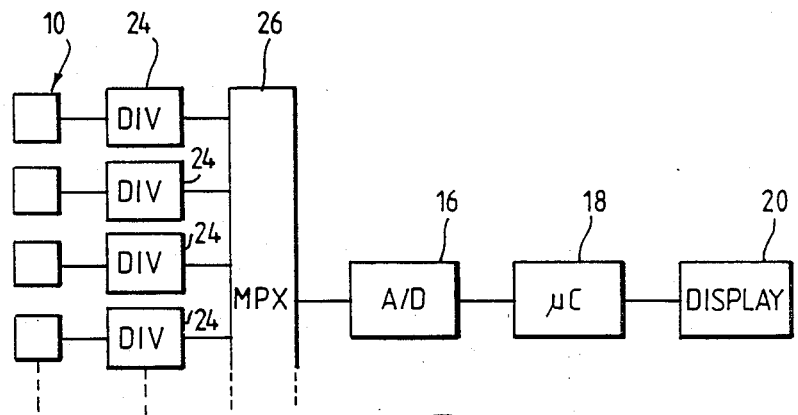
FIG. 2 is a block diagram of a second model "nose" in accordance with the invention.

A variation on the embodiment of FIG. 1, is illustrated in FIG. 2. In this case the load or divider element 14 of FIG. 1 is replaced by several such elements 24 each connected to a respective sensor. This allows different compensation responses to be used for different sensors if necessary. As before, the signals are multiplexed by a multiplexer 26 to generate a serial output for digitisation, analysis, and display.

With regard to the sensors forming the array 10 in the embodiments of FIG. 1 and FIG. 2, several different types may be used. In general, the apparatus described in this specification is not suited to conventional "electronic" sensors which use ionisation techniques to respond to a single substance (e.g. hydrogen in the case of sensors for fire risk alarms). Instead, sensors which respond to a number of substances are most suitable. Typically, such a sensor exhibits a change in resistance or capacitance when certain molecules are adsorbed. Sensors using tin oxide (Taguchi gas sensors) or conducting polymers undergo a resistance change, whilst those using Langmuir-Blodgett films depend on changes either in resistance or capacitance. Other sensors include chemically sensitive field-effect transistors (CHEMFETS) which depend on a change of potential brought about by the adsorption of molecules into the gate region of the device. A further possibility is the formation of an array of chemically sensitive semiconductor elements on a single silicon chip, together with circuits for signal processing and analysis.

Figure 3:
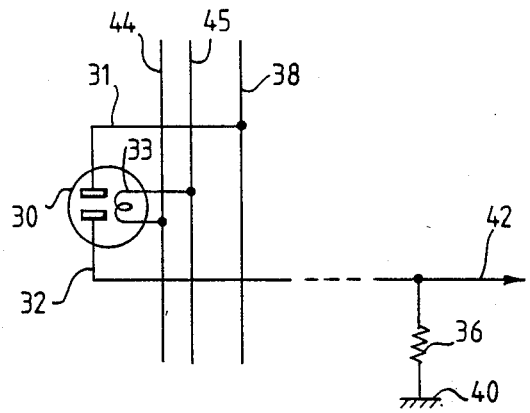
FIG. 3 is a circuit diagram of a sensor and a portion of an electrical input stage for use in the apparatus of FIG. 1 or FIG. 2.

As an illustration of the connection of a sensor to the following circuitry, FIG. 3 shows a Taguchi gas sensor 30 having a pair of sensing terminals 31, 32 and a heater coil 33. This sensor relies on the adsorption of molecules into a tin oxide layer deposited on a ceramic former, the oxide layer being connected in series between the terminals 31, 32. The sensor operates at a temperature in the region of 350° C., explaining the need for the heater coil. The sensing terminals 31, 32 are connected in a potential divider comprising the resistance represented by the oxide layer and a load resistance 36, the divider being coupled between a d.c. voltage rail 38 and a zero volts rail 40. Exposing the sensor to any of a variety of gases of sufficient concentration results in a change in resistance of the oxide layer and a consequent change in voltage at the divider tap 42. The value of the load resistor 36 is chosen to be of same order of the resistance of the oxide layer at the most linear part of the sensor's operating range. Any non-linearity can be compensated by subsequent circuitry with an inverse non-linear transfer function. Such circuitry may also include means for averaging the voltage obtained from the tap 42 to eliminate short term fluctuations arising from any rapid variations in substance concentrations. The heater coil 33 is provided with its own power supply connected across lines 44 and 45. The sensor array 10 may also be provided with means for compressing gases to increase their concentration, or means for diluting gases to decrease their concentration so as to bring the concentrations within a linear range of the sensors, or the combination of the sensors and the input circuitry.

With regard to the analysis of the sensor output signals, each combination of the outputs of one pair of sensors leads to one line in a calibration matrix. If the total number of lines in the matrix is i, then the matrix can be used to solve for the individual concentration of i constituent substances in a mixture of gases. The number of pairs of sensor outputs available from a device possessing N sensors is C(N,2), i.e. $N!/[2!(N-2)!]$. Thus, for three sensors, a 3-line matrix is obtained, for four sensors a 6-line matrix, and so on. The number of lines in the matrix corresponds to the maximum number of constituent substances for which a solution is possible. By using a mixture of fewer gases than this maximum number, redundancy may be built into the matrix equation and hence the error content reduced. It can be shown that an error in the overall response will introduce the greatest errors in the evaluation of concentration to those constituents which are least significant.

What is claimed is:

1. Apparatus for identifying, detecting or measuring gas or liquid borne substances, comprising:

a plurality of sensors arranged for simultaneous exposure to a sample to be analyzed, and electrical circuit means associated with the sensors and arranged to compensate for non-linear output versus substance concentration characteristics of the sensors, whereby each sensor, in combination with the circuit means, is operable to generate an electrical signal having a characteristic which is linearly related to the concentrations of a plurality of substances sensed by said each sensor, the circuit means including means for processing said electrical signals from said plurality of sensors to produce an electrical output indicative of an identity of the sample to be analyzed sensed by the sensors or of the presence and/or concentration of a particular substance or substances within said sample to be analyzed.

2. Apparatus according to claim 1, wherein each said sensor responds differently from others to preselected sample substances.

3. Apparatus according to claim 1, wherein at least some of the sensors exhibit non-linear output versus substance concentration characteristics and the circuit means is arranged to have a plurality of corresponding inverse non-linear characteristics to yield resultant linear characteristics.

4. Apparatus according to claim 1, wherein the circuit means includes at least one analog-to-digital converter for feeding digital representations of the sensor outputs to the processing means.

5. Apparatus according to claim 1, wherein the processing means is operable to provide an output indicative of substance concentration.

6. Apparatus for identifying, detecting or measuring gas or liquid borne substances, comprising:

a plurality of sensors arranged for simultaneous exposure to a substance, and electrical circuit means associated with the sensors and arranged to compensate for non-linear output versus substance concentration characteristics of the sensors, whereby each sensor, in combination with the circuit means, is operable to generate an electrical signal having a characteristic which is linearly related to the concentrations of a plurality of substances sensed by said each sensor, the circuit means including means for processing the said electrical signals from said plurality of sensors to produce an electrical output indicative of the identity of the substance or substances sensed by the sensors or of the presence and/or concentration of a particular substance or substances wherein each said sensor responds differently from others to preselected sample substances, and the processing means are operable to combine values representative of the said electrical signals on the basis of a series of linear equations.

7. Apparatus for identifying, detecting or measuring gas or liquid borne substances, comprising:

a plurality of sensors arranged for simultaneous exposure to a substance, and electrical circuit means associated with the sensors and arranged to compensate for non-linear output versus substance concentration characteristics of the sensors, whereby each sensor, in combination with the circuit means, is operable to generate an electrical signal having a characteristic which is linearly related to the concentrations of a plurality of substances sensed by said each sensor, the circuit means including means for processing the said electrical signals from said plurality of sensors to produce an electrical output indicative of the identity of the substance or substances sensed by the sensors or of the presence and/or concentration of a particular substance or substances, wherein the circuit means includes input means comprising at least one potential divider.

8. Apparatus for identifying, detecting or measuring gas or liquid borne substances, comprising:

a plurality of sensors arranged for simultaneous exposure to a substance, and electrical circuit means associated with the sensors and arranged to compensate for non-linear output versus substance concentration characteristics of the sensors, whereby each sensor, in combination with the circuit means, is operable to generate an electrical signal having a characteristic which is linearly related to the concentrations of a plurality of substances sensed by said each sensor, the circuit means including means for processing the said electrical signals from said plurality of sensors to produce an electrical output indicative of the identity of the substance or substances sensed by the sensors or of the presence and/or concentration of a particular substance or substances, wherein the circuit means includes input means comprising a potential divider coupled to the sensors via a multiplexing switch arrangement.

9. Apparatus for identifying, detecting, or measuring a gas or liquid borne substance or substances, comprising:

a plurality of sensors arranged to be simultaneously exposed to a sample to be analyzed;

electrical circuit means associated with the sensors including at least one analog-to-digital converter for generating digital electrical signals representative of electrical outputs of the sensors, and processing means coupled to the at least one analog-to-digital converter, programmed (a) to compensate for non-linear output versus substance concentration characteristics of the sensors thereby to generate signal values for each sensor which are linearly related to concentrations of substances sensed by the sensor, and (b) to perform a mathematical operation on the said values thereby to generate an electrical output indicative of the identity of the sample to be analyzed sensed by the sensors or of the presence of a preselected substance or substances in the sample to be analyzed.

10. A method of identifying, detecting or measuring a gas or liquid borne substance, comprising the steps of:

providing a plurality of substance sensors, each of which respond differently from each other to at least one preselected substance, exposing each of the sensors to the substance to be identified, detected or measured, feeding electrical outputs from the sensors to electrical circuitry to generate a plurality of electrical signal values related to substance concentration, compensating for non-linear output versus substance concentration characteristics of the sensors so that said signal values are linearly related to substance concentration, and performing a mathematical operation on the said signal values to generate information relating to the identity or presence of the substance to be identified or detected and/or the concentration of the said substance.

* * * * *